United States Patent
Zhao et al.

(10) Patent No.: US 8,386,045 B2
(45) Date of Patent: Feb. 26, 2013

(54) SYSTEMS AND METHODS FOR SELECTIVELY STIMULATING NERVE ROOTS

(75) Inventors: Weiying Zhao, Cupertino, CA (US);
Stephen Ruble, Lino Lakes, MN (US);
Allan C. Shuros, St. Paul, MN (US);
Jason J. Hamann, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 345 days.

(21) Appl. No.: 12/431,621

(22) Filed: Apr. 28, 2009

(65) Prior Publication Data

US 2009/0270935 A1    Oct. 29, 2009

Related U.S. Application Data

(60) Provisional application No. 61/048,742, filed on Apr. 29, 2008.

(51) Int. Cl.
*A61N 1/00* (2006.01)
(52) U.S. Cl. .................................................. 607/46
(58) Field of Classification Search .......... 607/117–118, 607/45–46
See application file for complete search history.

(56) References Cited

U.S. PATENT DOCUMENTS

| | | | |
|---|---|---|---|
| 6,104,957 A * | 8/2000 | Alo et al. | 607/46 |
| 6,258,086 B1 * | 7/2001 | Ashley et al. | 606/41 |
| 2001/0053885 A1 | 12/2001 | Gielen et al. | |
| 2002/0156513 A1 * | 10/2002 | Borkan | 607/117 |
| 2004/0116977 A1 * | 6/2004 | Finch et al. | 607/46 |
| 2004/0122477 A1 | 6/2004 | Whitehurst et al. | |
| 2004/0220621 A1 * | 11/2004 | Zhou et al. | 607/2 |
| 2005/0060006 A1 * | 3/2005 | Pflueger et al. | 607/43 |
| 2005/0107678 A1 | 5/2005 | Bowe | |
| 2006/0052837 A1 | 3/2006 | Kim et al. | |
| 2007/0021812 A1 | 1/2007 | Manning et al. | |
| 2007/0179579 A1 * | 8/2007 | Feler et al. | 607/117 |
| 2007/0250036 A1 | 10/2007 | Volk et al. | |
| 2008/0140169 A1 * | 6/2008 | Imran | 607/117 |
| 2008/0281372 A1 * | 11/2008 | Libbus et al. | 607/27 |
| 2009/0270960 A1 * | 10/2009 | Zhao et al. | 607/117 |

FOREIGN PATENT DOCUMENTS

| | | |
|---|---|---|
| WO | WO-02/092165 A1 | 11/2002 |
| WO | WO-2006/029257 A2 | 3/2006 |
| WO | WO-2006/133445 A2 | 12/2006 |
| WO | WO-2008/005142 A1 | 1/2008 |
| WO | WO-2009/134350 A2 | 11/2009 |

OTHER PUBLICATIONS

"International Application Serial No. PCT/US2009/002575, International Search Report mailed Dec. 1, 2009", 5 pgs.
"International Application Serial No. PCT/US2009/002575, Written Opinion mailed Dec. 1, 2009", 8 pgs.

(Continued)

*Primary Examiner* — Eric D. Bertram
*Assistant Examiner* — Roland Dinga
(74) *Attorney, Agent, or Firm* — Schwegman Lundberg & Woessner, P.A.

(57) ABSTRACT

Various system embodiments comprise an implantable lead, an implantable housing, a neural stimulation circuit in the housing, and a controller in the housing and connected to the neural stimulation circuit. The lead has a proximal end and a distal end. The distal end is adapted to deliver neural stimulation pulses to the ventral nerve root and the dorsal nerve root. The proximal end of the lead is adapted to connect to the housing. The neural stimulation circuit is adapted to generate neural stimulation pulses to stimulate the ventral nerve root or the dorsal nerve root using the implantable lead. The controller is adapted to control the neural stimulation circuit to deliver a neural stimulation treatment.

16 Claims, 12 Drawing Sheets

OTHER PUBLICATIONS

"European Application Serial No. 09739153.6, Office Action mailed May 27, 2011", 5 pgs.

Issa, Z. F., et al., "Thoracic spinal cord stimulation reduces the risk of ischemic ventricular arrhythmias in a postinfarction heart failure canine model", *Circulation*, 111(24), (Jun. 21, 2005), 3217-3220.

Lopshire, J. C., et al., "Spinal Cord Stimulation Improves Ventricular Function and Reduces Arrhythmias in a Canine Post-Infarction Heart Failure Model", *28th Annual Scientific Sessions of the Heart Rhythm Society* (*Heart Rhythm* 2007), (Abstract Only), (2007), 1 pg.

"European Application Serial No. 09739153.6, Response filed Dec. 2, 2011 to Office Action mailed May 27, 2011", 38 pgs.

\* cited by examiner

SYSTEMS AND METHODS FOR SELECTIVELY STIMULATING NERVE ROOTS

CROSS REFERENCE TO RELATED APPLICATIONS

This application claims the benefit of U.S. Provisional Application No. 61/048,742, filed on Apr. 29, 2008, under 35 U.S.C. §119(e), which is hereby incorporated by reference.

The following commonly assigned U.S. patent application is related and is incorporated by reference in its entirety: "Systems and Methods For Delivering Electric Current For Spinal Cord Stimulation," Ser. No. 61/048,736, filed Apr. 29, 2008.

TECHNICAL FIELD

This application relates generally to medical devices and, more particularly, to systems, devices and methods for selectively stimulating nerve roots.

BACKGROUND

Sympathetic over activation is involved in a variety of cardiovascular disease, such as ventricular arrhythmias, myocardial infarction (MI), heart failure (HF), etc. Therapies that are based on autonomic modulation have shown efficacy in a variety of cardiovascular diseases in both preclinical and clinical studies. The autonomic balance can be modulated to have more parasympathetic tone by stimulating parasympathetic targets or inhibiting sympathetic targets, and can be modulated to have more sympathetic tone by stimulating sympathetic targets or inhibiting parasympathetic targets.

Spinal cord stimulation has been proposed for a variety of treatments, such as pain control. One known system for delivering electrical stimulation to neural targets in and around the spinal cord uses a lead inserted one-dimensionally into the dorsal epidural space of the spinal cord.

SUMMARY

Various system embodiments comprise an implantable lead, an implantable housing, a neural stimulation circuit in the housing, and a controller in the housing and connected to the neural stimulation circuit. The lead has a proximal end and a distal end. The distal end is adapted to deliver neural stimulation pulses to the ventral nerve root and the dorsal nerve root. The proximal end of the lead is adapted to connect to the housing. The neural stimulation circuit is adapted to generate neural stimulation pulses to stimulate the ventral nerve root or the dorsal nerve root using the implantable lead. The controller is adapted to control the neural stimulation circuit to deliver a neural stimulation treatment.

Various system embodiments comprise means for stimulating nerve roots including means for stimulating a ventral nerve root and means for stimulating a dorsal nerve root, and further include means for independently controlling stimulation of the ventral nerve root and stimulation of the dorsal nerve root.

According to a method embodiment, a neural stimulation lead fed vertically through a dorsal epidural space of a human and at least partially wrapped around a spinal cord is used to deliver electrical stimulation pulses to at least one of: a ventral nerve root to stimulate or efferent sympathetic activity from the ventral nerve root; or a dorsal nerve root to stimulate or inhibit afferent sympathetic activity from the dorsal nerve root.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1A:
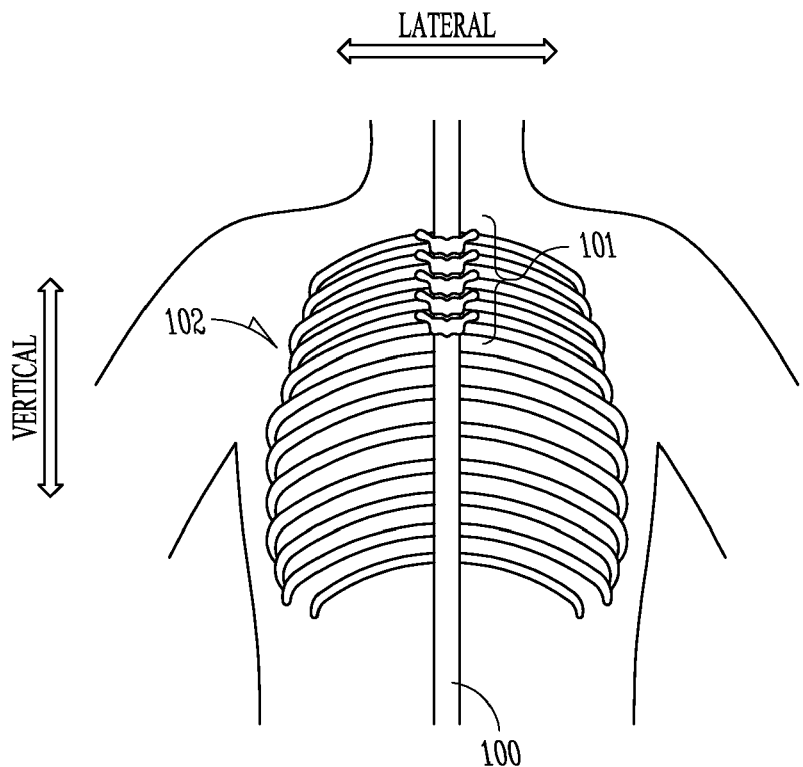
FIG. 1A illustrates a spinal column, including the T1-T5 vertebrae, from a posterior or dorsal perspective.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

A known spinal cord stimulation system contains a straight lead body with multiple electrodes, which only allows for one-dimensional movement along the spinal cord. The vertical, one-dimensional access within the epidural space limits the ability of the device to selectively stimulate neural pathways, to position the electrodes with respect to the neural targets in a desired position to promote a desired efficacy of the stimulation, and to avoid loss of nerve capture due to migration or movements of the lead in the epidural space. Some issues with this lead design include lead migration and the inability to precisely stimulate the dorsal and ventral nerve root.

Various embodiments that provide neural stimulation treatment selectively stimulate sympathetic afferent and/or efferent neurones on the thoracic spinal cord. The system, device and method provide a versatile way to stimulate neural targets in the spinal cord region. Sympathetic modulation (inhibition or activation of sympathetic activity) treats a variety of cardiovascular disease with abnormal sympathetic activity. The neural stimulation is capable of being implemented in treatments for pain, heart failure, arrhythmia, angina, and the like. Various embodiments activate sympathetic afferent (e.g. relatively low frequency dorsal horn stimulation) or activate sympathetic efferent (e.g. relatively low frequency ventral horn stimulation) or inhibit or block sympathetic efferent (e.g. relatively high frequency ventral horn stimulation). Some embodiments test and appropriately modify the therapy delivery by testing the sympathetic response (e.g., heart rate and blood pressure changes) and using the electrodes which are operationally-positioned to stimulate the selected neurons.

Various embodiments that deliver electrodes for spinal cord stimulation provide a steerable design, which is capable of selectively stimulating sympathetic afferent pathways in the dorsal nerve root, sympathetic efferent pathways in the ventral nerve root, or both sympathetic afferent and efferent pathways. The lead can be moved vertically up and down along the spinal cord. Once the targeted region is reached, such as in the T1-T5 region, the lead body is capable of being steered to bend and curve around the spinal cord. Some embodiments target other regions of the spinal column, such as various regions in the cervical, thoracic or lumbar areas. Some embodiments cause the lead to contract around at least a portion of the spinal cord or other structure of the spinal column. The contraction is appropriate to fix the electrodes in position with respect to the spinal cord without providing an undesirably high force against the spine. Various lead embodiments provide multiple electrodes along both the ventral and dorsal horn of the spinal column, allowing the electric current to be delivered to either activate sympathetic afferent (low frequency dorsal horn stimulation) or activate sympathetic efferent (low frequency ventral horn stimulation) or electric blocking sympathetic efferent (high frequency ventral horn stimulation). Some embodiments test and appropriately modify the therapy delivery by testing the sympathetic response (e.g., heart rate and blood pressure changes) and using the electrodes which are operationally-positioned to stimulate the selected neurons.

Physiology

Provided below is a brief discussion of some diseases capable of being treated using the present subject matter and the nervous system. This discussion is believed to assist a reader in understanding the disclosed subject matter.

Diseases

The present subject matter can be used to prophylactically or therapeutically treat various diseases by modulating autonomic tone. Examples of such diseases or conditions include hypertension, cardiac remodeling, and heart failure.

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

Following myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction (decompensation). It has been shown that the extent of ventricular remodeling is positively correlated with increased mortality in post-MI and heart failure patients.

Heart failure (HF) refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease. Heart failure patients have reduced autonomic balance, which is associated with LV dysfunction and increased mortality.

Nervous System

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent nerves convey impulses toward a nerve center, and efferent nerves convey impulses away from a nerve center.

The heart rate and force is increased when the sympathetic nervous system is stimulated, and is decreased when the sympathetic nervous system is inhibited (the parasympathetic nervous system is stimulated). Cardiac rate, contractility, and excitability are known to be modulated by centrally mediated reflex pathways. Baroreceptors and chemoreceptors in the heart, great vessels, and lungs, transmit cardiac activity through vagal and sympathetic afferent fibers to the central nervous system. Activation of sympathetic afferents triggers reflex sympathetic activation, parasympathetic inhibition, vasoconstriction, and tachycardia. In contrast, parasympathetic activation results in bradycardia, vasodilation, and inhibition of vasopressin release. Among many other factors, decreased parasympathetic or vagal tone or increased sympathetic tone is associated with various arrhythmias genesis, including ventricular tachycardia and atrial fibrillation.

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other.

Neural stimulation can be used to stimulate nerve traffic or inhibit nerve traffic. An example of neural stimulation to stimulate nerve traffic is a lower frequency signal (e.g. within a range on the order of 20 Hz to 50 Hz). An example of neural stimulation to inhibit nerve traffic is a higher frequency signal (e.g. within a range on the order of 120 Hz to 150 Hz). Other methods for stimulating and inhibiting nerve traffic have been proposed.

Modulation of the autonomic nervous system has potential clinical benefit in preventing remodeling and death in heart failure and post-MI patients. Electrical stimulation can be used to inhibit sympathetic nerve activity and reduce blood pressure by decreasing vascular resistance. Sympathetic inhibition, which increases parasympathetic tone, has been associated with reduced arrhythmia vulnerability following a myocardial infarction, presumably by increasing collateral perfusion of the acutely ischemic myocardium and decreasing myocardial damage.

Spinal Cord

Figure 1B:
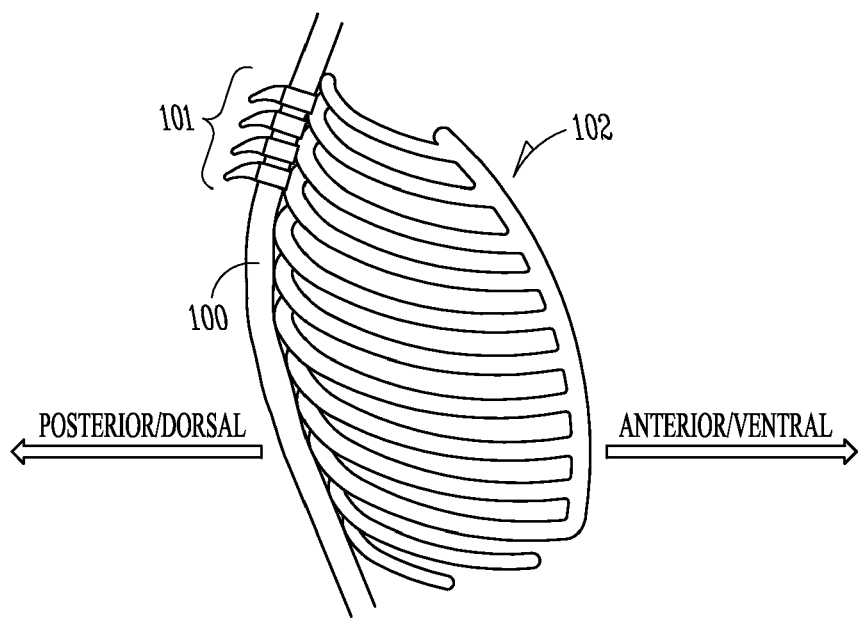
FIG. 1B illustrates a side view of the spinal column.

FIG. 1A illustrates a spinal column 100, including the T1-T5 vertebrae 101, and further illustrates ribs 102 from a posterior or dorsal perspective. FIG. 1B illustrates a side view of the spinal column, including the T1-T5 vertebrae 101 of the column, and the ribs 102. These figures also illustrate a lateral axis, a vertical axis in the cranial (up) or caudal (down) direction, and a posterior or dorsal direction and an anterior or ventral direction.

The spinal column includes cervical, thoracic and lumbar areas. Vertebrae form the building blocks of the spinal column and protect the spinal cord. T1-T5 are the uppermost (cranial) portion of the thoracic area of the spinal column. Projections from T1-T5 innervate the heart. The spinal projections from T1-T5 are sympathetic. Increased efferent sympathetic activity increases heart rate and contractility. Afferent (e.g. pain signals) for the heart tissue also go throughout spinal segments T1-T5. Various embodiments target the T1-T5 region for cardiovascular disease applications. Other regions may be targeted for other applications (e.g. treatment for hypertension, diabetes, obesity, etc.).

Figure 2:
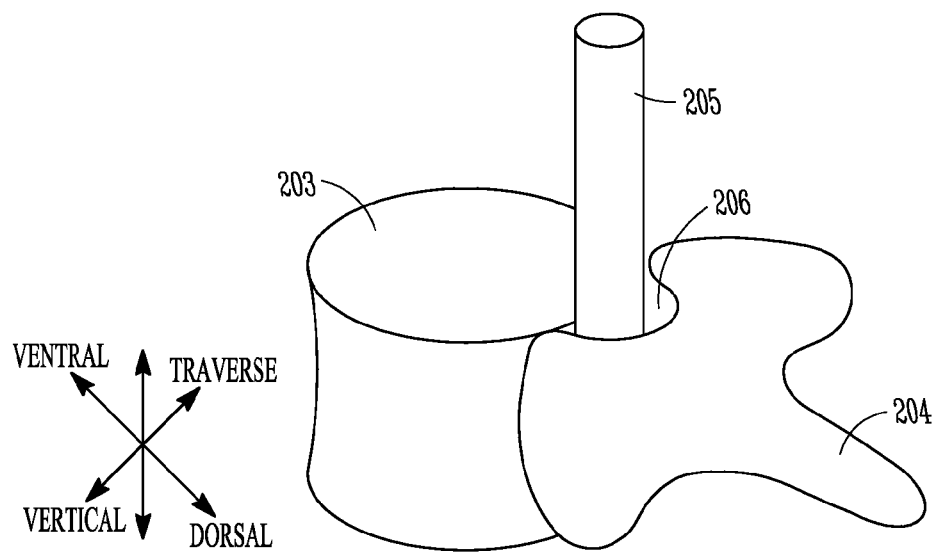
FIG. 2 illustrates a perspective view of a portion of the spinal column.

FIG. 2 illustrates a perspective view of a portion of the spinal column. As illustrated, the vertebrae includes a vertebral body 203 and a bony ring 204 attached to the vertebral body 203. The stacked vertebrae provide a vertebral canal that protects the spinal cord 205. The spinal cord is nerve tissue that carries neural messages between the brain and parts of the body. Nerve roots branch off and exit the spine on both sides through spaces between the vertebra. The spinal cord is surrounded by dura matter, which holds spinal fluid that surrounds the spinal cord. The space between the walls and the dura matter of the vertebral canal is referred to as epidural space 206. Some embodiments of the present subject matter steer a lead through the dorsal epidural space 206 to the T1-T5 region, and some embodiments steer a catheter through the dorsal epidural space to the T1-T5 region.

Figure 3:
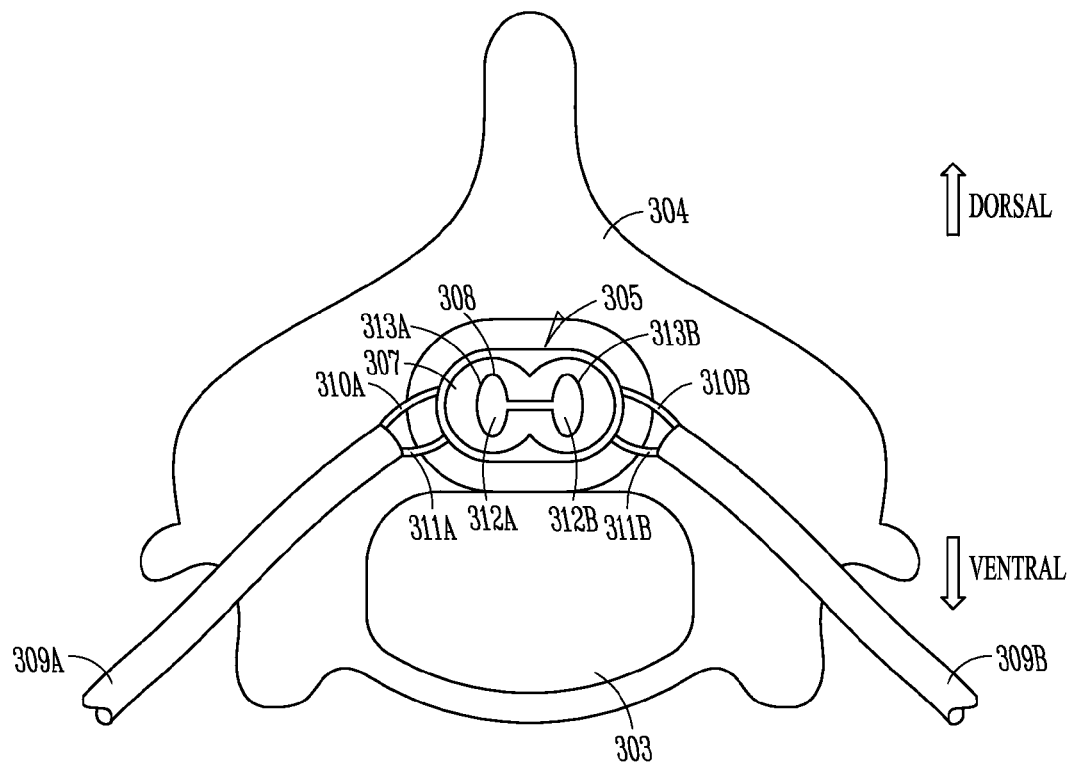
FIG. 3 illustrates a top view of a cross section of the spinal column.

FIG. 3 illustrates a top view of a cross section of a vertebra in the spinal column. The vertebra includes a vertebral body 303 and a bony ring 304 that includes the spinous process. The vertebrae provide a spinal canal that contains the spinal cord. The illustrated spinal cord includes white matter 307 and gray matter 308. Spinal nerves 309A, 309B extend from the sides of the spinal column. Each spinal nerve 309A, 309B has a dorsal nerve root 310A, 310B and a ventral nerve root 311A, 311B. The front or ventral gray column of the spinal cord is referred to as the ventral horn 312A, 312B, which is a longitudinal subdivision of gray matter in the anterior part of each lateral half of the spinal cord that contains neurons giving rise to motor fibers of the ventral roots of the spinal nerves. The posterior gray column of the spinal cord is referred to as the dorsal horn 313A, 313B, which is a longitudinal subdivision of gray matter in the dorsal part of each lateral half to the spinal cord that receives terminals from some afferent fibers of the dorsal roots of the spinal nerves. The ventral root 311A, 311B is the efferent motor root of a spinal nerve. The dorsal root 310A, 310B is the afferent sensory root of the spinal nerve. The ventral root joins with the dorsal root to form a mixed spinal nerve 309A, 309B. The distal end of the dorsal root includes the dorsal root ganglion which contains the neuron cell bodies of the nerve fibers conveyed by the root.

The afferent sympathetic pathway includes neuron bodies in the dorsal root ganglia, and neuron bodies in the dorsal horn. The efferent sympathetic pathway includes preganglionic motor neuron bodies in the intermediolateral column of the spinal cord from to T4/T5, and postganglionic motor neuron bodies in superior, middle and inferior cervical ganglias and in cell T1 thoracic ganglias from T1 to T4/T5. Various embodiments modulate sympathetic efferent and afferent activity by delivering electric current to selected regions of the thoracic spinal cord. Some embodiments provide a three-dimensional, steerable lead design. The lead can be moved up and down along the spinal column. At the targeted region, the lead body is capable of being steered to bend and curve around the spinal cord. This lead placement provides multiple electrodes located along both the ventral and dorsal horn of the spinal cord. Selected electrodes are used to selectively modulate afferent, efferent or both afferent and efferent pathways. Thus, a desired therapy is provided by choosing electrodes that are closest to sympathetic neurons.

Figure 4:
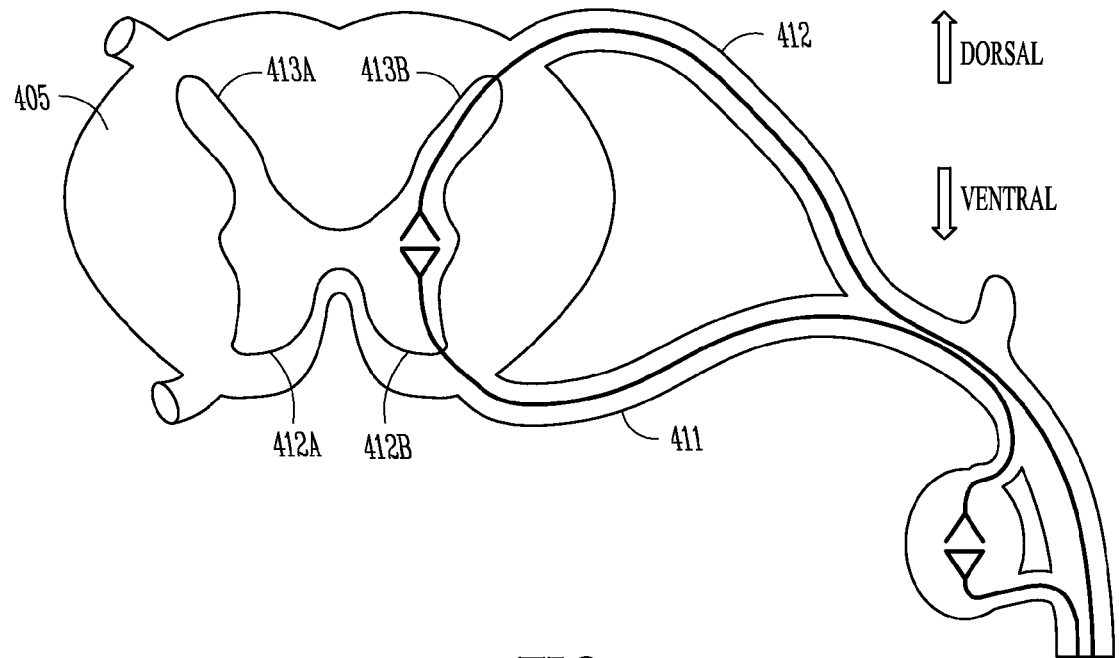
FIG. 4 illustrates an embodiment of a method for implanting a lead for use in delivering spinal cord stimulation.

FIG. 4 illustrates sympathetic pathways extending from ventral and dorsal nerve roots. The gray matter of the spinal cord 405 includes ventral horns 412A, 412B and dorsal horns 413A, 413B. The ventral root 411 is the efferent motor root of a spinal nerve. The dorsal root 412 is the afferent sensory root of the spinal nerve. The ventral root joins with the dorsal root to form a mixed spinal nerve.

Figure 5:
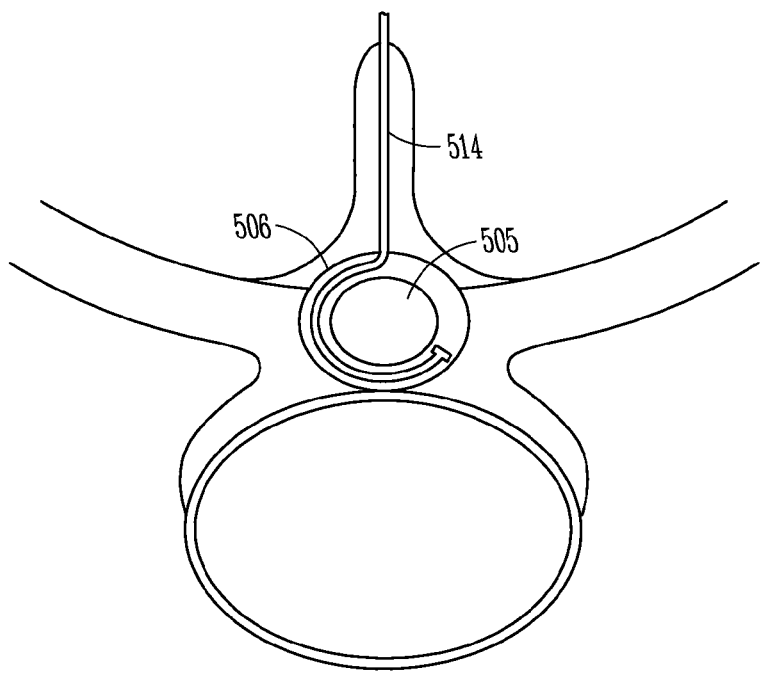
FIG. 5 illustrates sympathetic pathways extending from ventral and dorsal nerve roots.

FIG. 5 illustrates an embodiment of a method for implanting a lead for use in delivering spinal cord stimulation. The patient can sit or lie on their side in a position of back flexion to open the intervertebral spaces. Depending on the implant location, the appropriate lumbar space is identified using Tuffier's line as a reference point. Using a sterile technique the spinal lead introducer is inserted in the midline, while aiming cranially. As the needle is pushed forward, there is resistance as it passes through the ligamentum flavae. The loss of resistance is evidence that the epidural space has been penetrated. Once in the epidural space 506, the lead 514 can be deployed through the introducer and then passed into the epidural space, and then up to the T1-T5 region and around at least a portion of the spinal cord 505.

Figure 6:
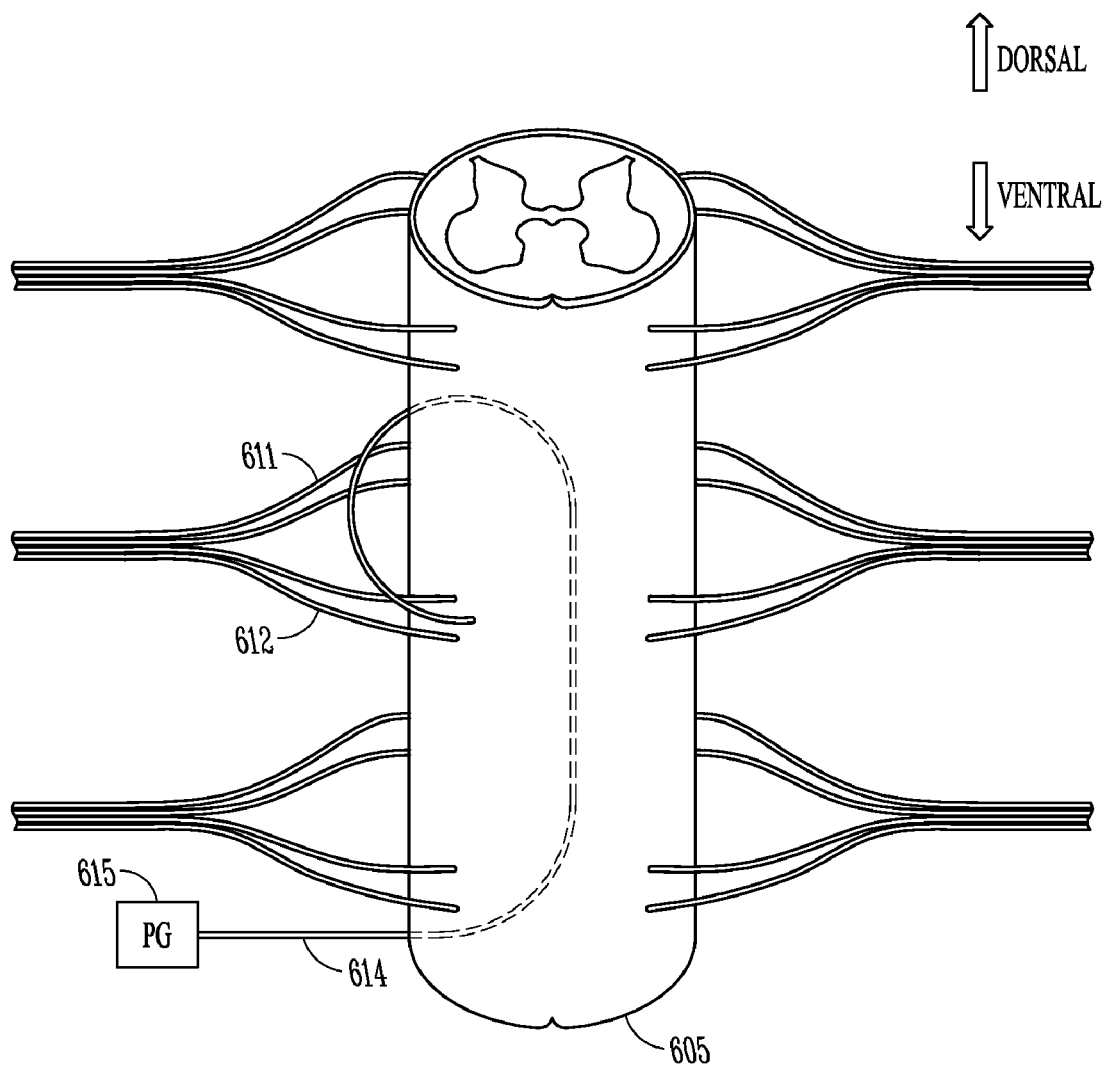
FIG. 6 illustrates a portion of the spinal cord, with nerve roots extending from three vertebral locations, and further illustrates a neural stimulation lead fed through the dorsal epidural space and at least partially around the spinal cord to operationally set electrodes in place to stimulate and/or inhibit activity in the dorsal and ventral nerve roots, according to various embodiments.

FIG. 6 illustrates a portion of the spinal cord 605, with nerve roots extending from three vertebral locations, and further illustrates a neural stimulation lead 614 fed through the dorsal epidural space (behind the illustrated cord 605) and least partially around the spinal cord to operationally set electrodes in place to stimulate and/or inhibit activity in the dorsal and ventral nerve roots 611, 612, according to various embodiments. The pulse generator 615 can be implanted in an appropriate location, such as in an abdominal region or in or just above the buttocks. During the implantation procedure, the proximate end of the lead can be connected to an external device used to generate stimulation pulses and monitor the efficacy of the lead placement.

Figure 7:
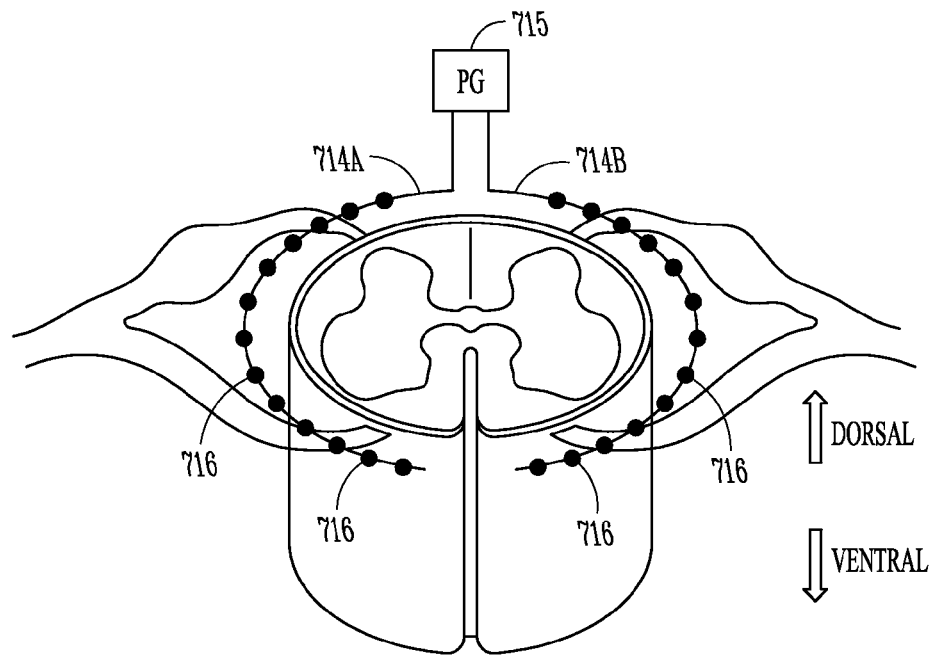
FIG. 7 illustrates a multi-lead embodiment to stimulate dorsal and ventral nerve roots on contralateral sides of the spinal cord.

FIG. 7 illustrates a multi-lead embodiment to stimulate dorsal and ventral nerve roots on contralateral sides of the spinal cord. The illustrated figure shows two leads exiting from a pulse generator 715. One lead 714A is directed around a first side, and a second lead 714B is directed around a second side. Electrodes on each lead are placed operationally in position with respect to the nerve root(s) to stimulate the neural target(s) and elicit the desired effect(s).

Figure 8:
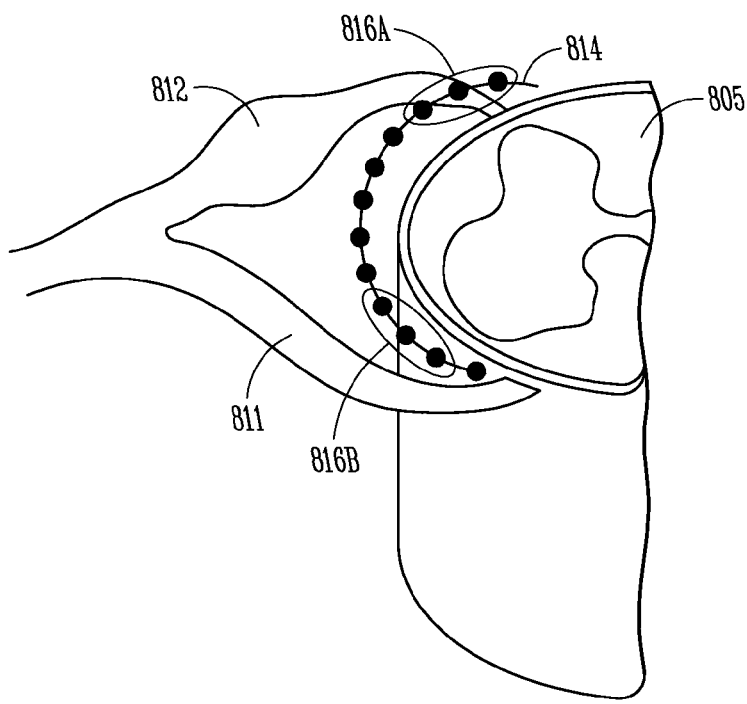
FIG. 8 illustrates multiple electrodes on a lead wrapped at least partially around the spinal cord, where at least some of the electrodes are operationally positioned for use to stimulate the dorsal nerve root and some of the electrodes are operationally positioned for use to stimulate the ventral nerve root.

FIG. 8 illustrates multiple electrodes on a lead 814 wrapped at least partially around the spinal cord 805, where at least some of the electrodes 816A are operationally positioned for use to stimulate the dorsal nerve root 812 and some of the electrodes 816B are operationally positioned for use to stimulate the ventral nerve root 811. Each lead includes a plurality of electrodes that are adapted to be combined to generate various stimulation vectors. Thus, an appropriate combination of electrodes can be used to generate a stimulation field that effectively stimulates the desired neural target(s), and in some embodiments, avoid possible undesired effects of neural stimulation.

Some benefits of the present subject matter include more therapy choices, including efferent, afferent, and both efferent and afferent targets. Some embodiments provide simultaneous afferent and efferent modulation. For example, chronic intermittent sympathetic efferent stimulation could be used to alter the progression of HF. Meanwhile, a sensed tachy event could trigger sympathetic afferent stimulation to inhibit the occurrence of a ventricular arrhythmia. Some embodiments provide the capability of altering afferent and efferent modulation to provide a more robust therapy. For example, in HF patients, chronic sympathetic afferent stimulation and chronic sympathetic efferent block or inhibition could be applied in an alternating order to inhibit sympathetic activity, while also preventing desensitization. Some embodiments provide the ability to monitor and adjust the stimulation to provide and/or maintain a desired efficacy (capture neural target and/or avoid or abate side effects) of the therapy. Some lead embodiments promote stable lead placement, which prevents or abates lead migration and movement.

Some embodiments of the present subject matter provide a treatment for tachyarrhythmia. For example, some embodiments deliver sympathetic afferent stimulation at the dorsal horn of the spinal cord with a relatively low frequency to reflexively inhibit sympathetic activity; and some embodiments deliver direct sympathetic efferent inhibition with a relatively high frequency stimulation at the ventral horn of the spinal column. Some embodiments of the present subject matter provide a treatment for heart failure. For example, some embodiments enhance sympathetic activity periodically with chronic intermittent efferent stimulation at the ventral horn of the spinal column with a relatively low frequency. Some embodiments inhibit or block sympathetic efferent activity, either chronically or intermittently, using a high frequency electrical stimulation at the ventral horn of the spinal cord.

Lead/Catheters

An embodiment uses a steerable delivery catheter (e.g. using stereotaxis magnetic guidance) or other guidance means to aid in positioning the lead in the targeted region of the epidural space. Some catheter embodiments are steerable in two axes (vertical, also referred to as cranial/caudal axis, and lateral axis). Some lead embodiments have a distal "J" biased tip designed to wrap around the spinal cord when the lead is deployed from the delivery catheter to the targeted region. The J-biased tip aids in retaining the electrodes in place, avoiding or abating lead migration. Additionally, the J-biased tip maintains contact with the spinal column, keeping the stimulation electrodes desirably close to the ventral and/or dorsal nerve roots. The delivery catheter is then peeled or cut away from the lead, leaving the lead in position.

An embodiment uses a steerable stimulation lead to aid in positioning the lead in the targeted region of the epidural space. Some lead embodiments are steerable in two axes (vertical or cranial/caudal axis, and lateral axis). Some lead embodiments are adapted to be locked or fixed in a fixed position, aiding in retaining the electrodes in place and maintaining contact with the spinal column, keeping the stimulation electrodes desirably close to the ventral and/or dorsal nerve roots. For example, some embodiments use a chuck to hold the lead in position. Other designs can be used to fix or stabilize the position of the lead. A position fixation apparatus on a proximal end of the lead can be used to maintain a shape and position of a distal end of the lead.

Figure 9:
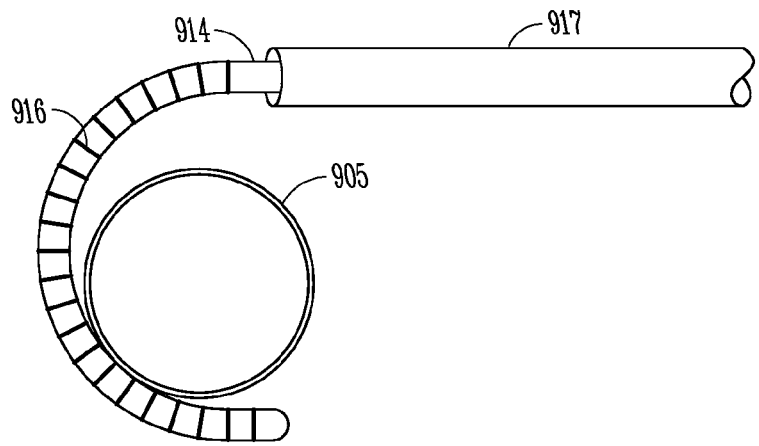
FIG. 9 illustrates an embodiment that includes a preformed lead made with a material having a shape memory, where the lead resumes its preformed shape to at least partially wrap around the spinal cord when the lead exits a catheter used to deliver the lead to the stimulation site.

FIG. 9 illustrates an embodiment that includes a pre-formed lead made with a material having a shape memory, where the lead 914 resumes its preformed shape to at least partially wrap around the spinal cord 905 (or potentially some other structures of the spinal column) when the lead exits a catheter 917 used to deliver the lead to the stimulation site. The illustrated portion of the pre-formed lead has a plurality of electrodes 916, various combinations of which can be selected to generate a desired neural stimulation field to stimulate a desired neural target. The lead is designed with appropriate material characteristics to provide an appropriate force when contracting back into its preformed shape. In some embodiments, the force of contraction is sufficient to fix the lead in position or to discourage lead migration.

Figure 10A:
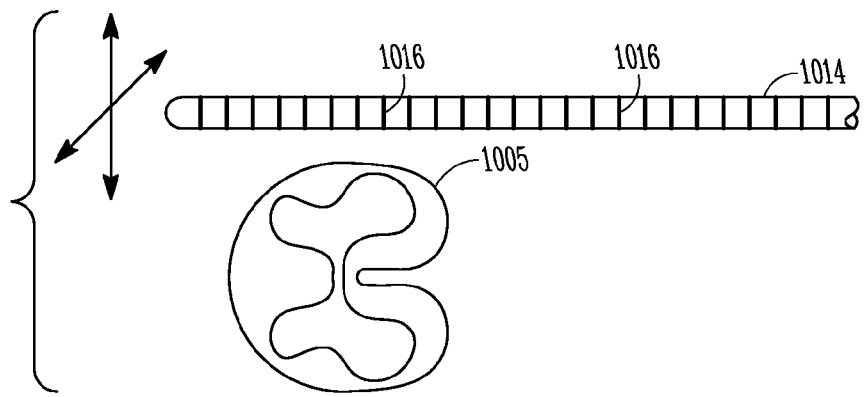
FIGS. 10A and 10B illustrate a steerable lead embodiment used to place stimulation electrodes in operational position to stimulate ventral and dorsal nerve leads.
Figure 10B:
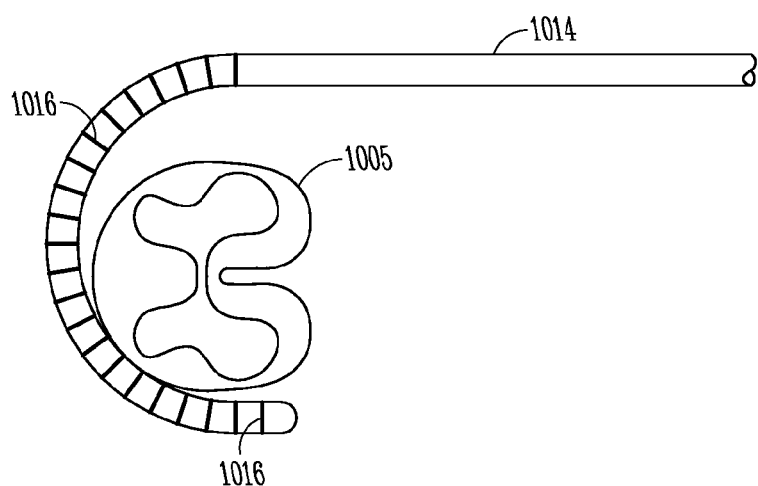

FIGS. 10A and 10B illustrate a steerable lead embodiment used to place stimulation electrodes in operational position to stimulate ventral and dorsal nerves, the illustrated lead 1014 includes a plurality of electrodes 1016. As is illustrated in an embodiment below, the lead is designed to be steered in at least two directions, to allow the lead to be steered from the dorsal epidural space around at least a portion of spinal cord 1005 to stimulate the nerve root(s). A steering tendon or guy wire can be used to contract the lead around the spinal cord, fixating the electrodes in operational position to stimulate the ventral and/or dorsal nerve roots.

Figure 11A:
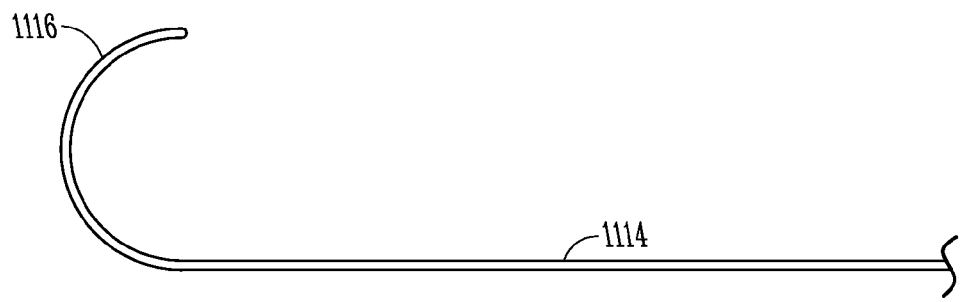
FIGS. 11A-11C illustrate an embodiment of a steerable lead.
Figure 11B:
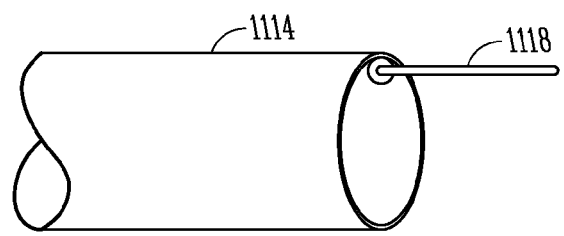
Figure 11C:
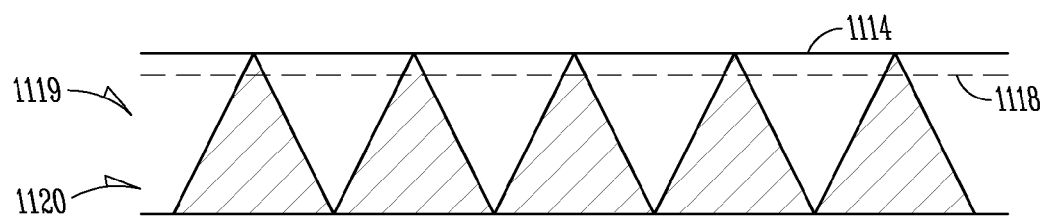

FIGS. 11A-11C illustrate an embodiment of a steerable lead. The lead body 1114 includes a distal end 1116. A lumen adapted to receive a steering tendon 1118 is in the lead body 1114. The lead body 1114 includes a compressible or expandable side 1119 and a noncompressible or expandable side 1120. The steering tendon is appropriately connected to the compressible or expandable side to control the compression or expansion of that side. When the lead is implanted, the lead is steered by appropriately controlling the tendon.

Figure 12:
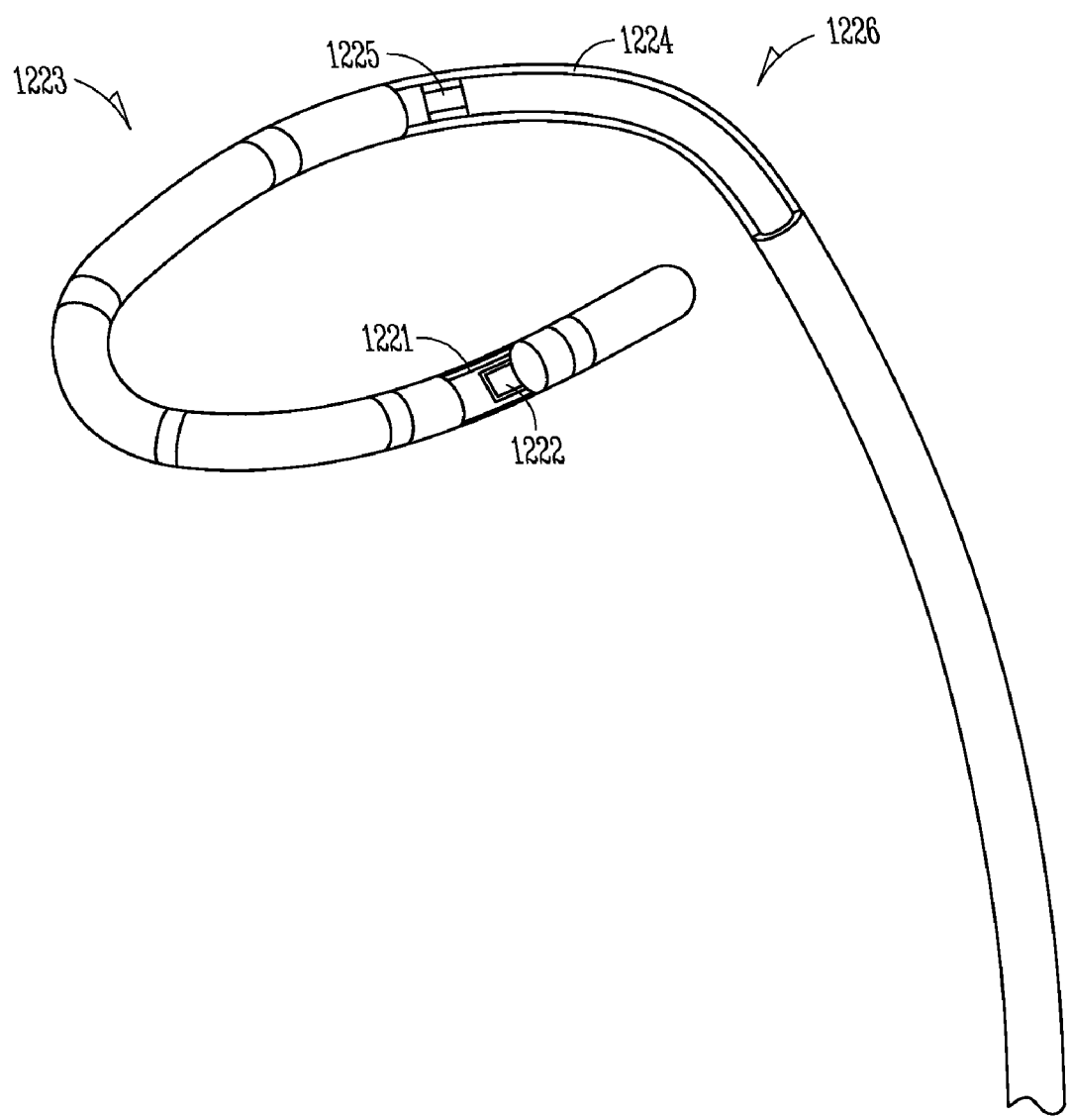
FIG. 12 illustrates a steerable catheter embodiment used to deliver a lead to place stimulation electrodes from the lead in operational position to stimulate ventral and dorsal nerve leads.

FIG. 12 illustrates a steerable catheter embodiment used to deliver a lead to place stimulation electrodes from the lead in operational position to stimulate ventral and dorsal nerve leads. A first steering tendon 1221 is attached to a first anchor member 1222 located at a distal portion of the pre-formed distal end 1223. A second steering tendon 1224 is attached to a second anchor member 1225 located distal to the deflection area 1226.

The anchor members 1222, 1225 can be constructed using various materials and construction methods known in the art, including simply bonding a distal part of the tendon to the shaft. In the illustrated configuration, the anchor members 404, 408 are formed of stainless steel rings to which steering tendons can be welded or soldered. The steering tendons may be attached to the anchor members using a mechanical interference fit such as a crimp or a stop member. The steering tendons are typically made of metallic (e.g. stainless steel) members such as solid wire, braided wire, or ribbon material. It is possible to form tendons from non-metallic members such as high strength composite members (e.g. Kevlar, carbon fiber).

Some embodiments embed the anchor members within the walls of the lead shaft 1214 during shaft construction. In some embodiments, the anchor members are adhered to the inner wall of the lead shaft 1214 by adhesive bonding or hot melting the shaft material. Hot melting may be performed by heating the anchor members while in intimate contact with the inner walls of the shaft. Another method of attaching the anchor members involves butting the bands against a support structure of the shaft 102 such as a reinforcement cage or braid.

Figure 13A:
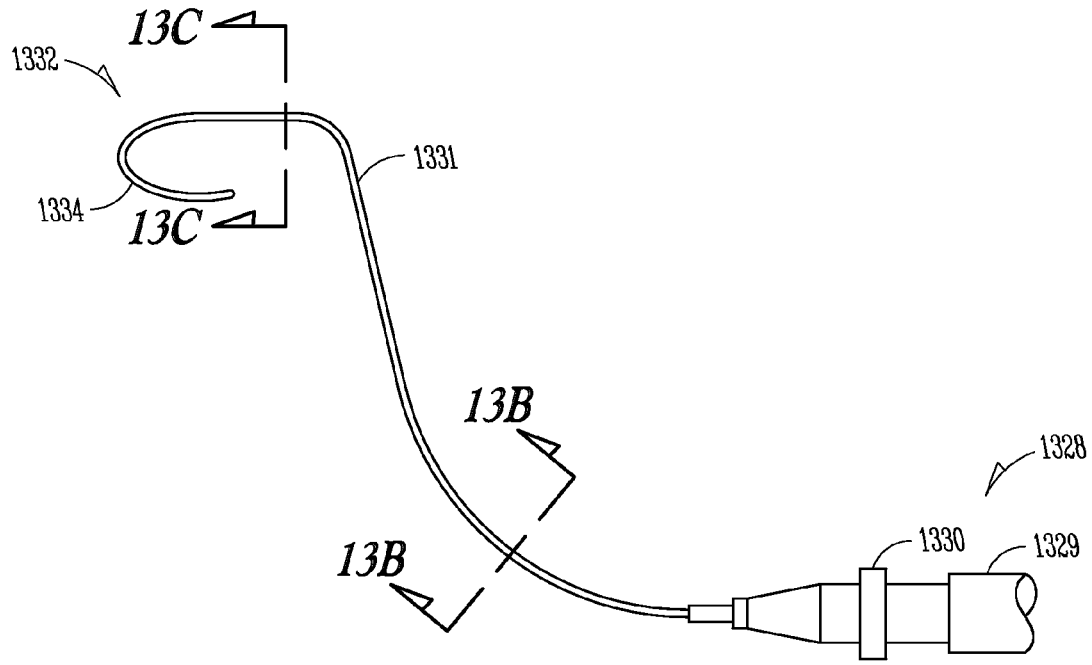
FIGS. 13A-13C illustrate an embodiment of a steerable catheter.
Figure 13B:
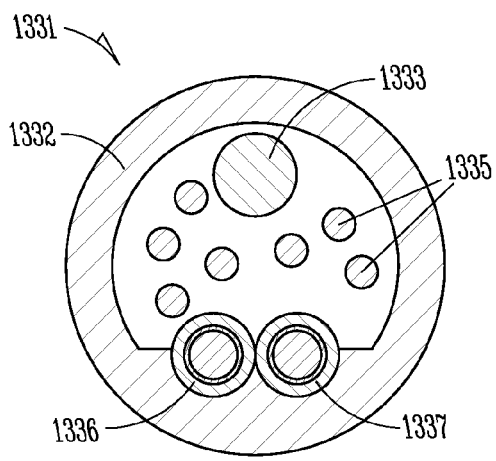
Figure 13C:
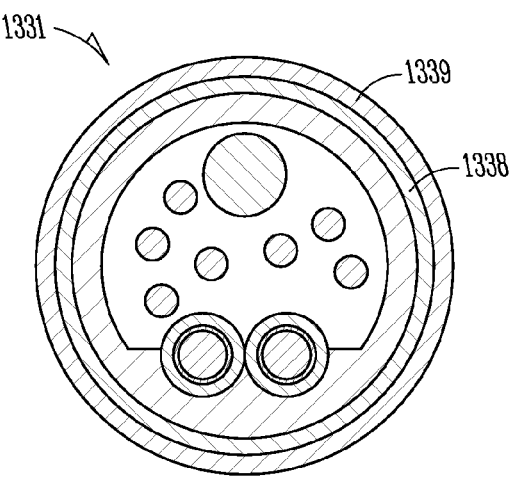

FIGS. 13A-13C illustrate an embodiment of a steerable catheter. FIG. 13A is an external view of the catheter including a proximal handle assembly 1328. The proximal handle assembly 1328 typically includes a grip 1329 and a steering member 1330. The handle assembly 1328 can be constructed by principles known in the art, such as described in U.S. Pat. Nos. 6,096,036 and 6,270,496, which are hereby incorporated by reference in their respective entireties.

FIG. 13B is a cross section of a distal part of the catheter shaft roughly corresponding to section B-B in FIG. 13A. A shaft embodiment 1331 includes a wall 1332 formed of polymer, typically a high durometer Pebax material. The shaft wall encloses a stylet 1333, typically made of a resilient, shape-memory member such as a wire formed of nitinol wire or other superelastic alloy. A nitinol stylet is preshaped by heating the stylet while it is being constrained in the desired shape. A stylet formed in this way is then inserted into the shaft to impart the preformed shape at the distal end 1334 of the shaft 1331. The stylet is typically affixed at or near the tip of the shaft to prevent migration of the stylet within the catheter during use.

In the illustrated figures, the wall of the shaft also encloses conductors 1335 coupled to the electrodes. Also shown within the shaft are the steering tendons 1336, 1337. The steering tendons are disposed within lumens, which are typically formed of a lubricous material such as PTFE and may be affixed to an inner surface of the shaft wall.

FIG. 13C shows a cross section of a proximal part of the catheter shaft 1331. The layout of the shaft is similar to that seen in FIG. 13B, and additionally shows a reinforcing member 1338 and an outer casing 1339. The reinforcing member can include a braid, cage, ribbon, or other reinforcing member that provides axial and torsional stiffness to the shaft while still allowing a reasonable amount of bending in the shaft. The outer casing may be made of a Pebax material having a similar durometer as the shaft wall, or may be made of a different material having unique protective and/or lubricous properties. The differences between the distal and proximal cross sections (e.g. inclusion of a proximal support member) as seen in FIGS. 13B and 13C result in the proximal portion having greater stiffness than the distal portion. Other variations in stiffness may also be advantageously induced along portions of the flexible shaft. To vary stiffness of the shaft, the bending properties of the shaft wall may be changed (e.g. the durometer of the polymeric materials) or the stylet characteristics (e.g. outer diameter or cross section) can be varied along the shaft length. Varying the stiffness along the length of the shaft can beneficially enhance the deflectability of the steered sections or to tune the stiffness of the distal end to minimize the risk of trauma.

A number of electrode configurations can be used. The illustrations included herein are provided as examples, and are not intended to be an exhaustive listing of possible configurations.

Figure 14:
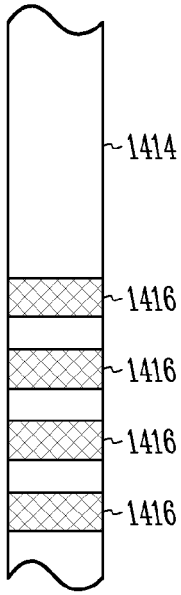
FIG. 14 illustrates a lead embodiment with a plurality of ring electrodes.

FIG. 14 illustrates a lead embodiment with a plurality of ring electrodes. The figure illustrates an embodiment of a lead 1414 with annular stimulation electrodes 1416 that form an electrode region, such as used to selectively stimulate the ventral nerve root or dorsal nerve root, according to various embodiments. Any one or combination of the annular stimulation electrodes can be used to deliver the neural stimulation to the desired neural target.

Figure 15A:
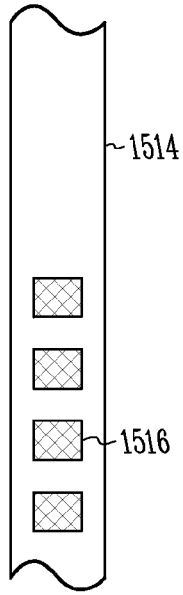
FIGS. 15A-15B illustrate a lead embodiment with multiple electrodes on a circumference of the lead.
Figure 15B:
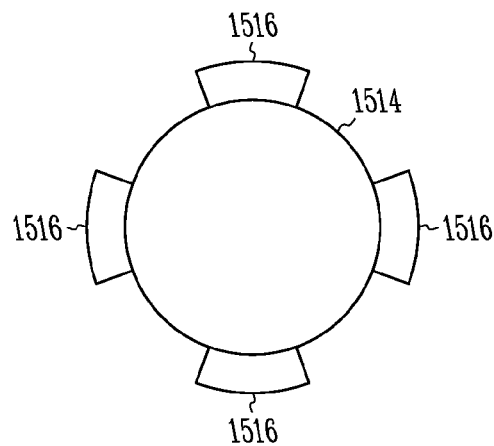

FIGS. 15A-15B illustrate a lead embodiment with multiple electrodes on a circumference of the lead. The illustrated electrodes 1516 do not circumscribe the lead 1514. Thus, a subset of the illustrated electrodes can be selected to provide directional stimulation. For example, the lead may twist or rotate as it is fed into position, and it may be desired to stimulate a neural target on one side of the lead without stimulating other nerves or tissue on the other sides of the lead. For example, root nerves extending from one vertebrae can be stimulated without stimulating root nerves extending from other vertebrae. A neural stimulation test routine can cycle through the available electrodes for use in delivering the neural stimulation to determine which subset of electrodes are facing toward the neural target. FIG. 15B illustrates an example with four electrodes separated around the lead, approximately 90 degrees apart. Other electrode arrangements and spacing can be used, such as, by way of example and not limitation, 2 electrodes spaced around the circumference approximately 45 degrees apart, approximately 90 degrees apart or approximately 180 degrees apart; or 3 electrodes spaced around the circumference approximately 120 degrees, approximately 60 degrees or approximately 30 degrees apart.

Figure 16A:
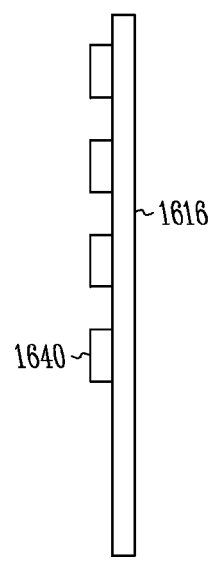
FIGS. 16A-16B illustrate a lead embodiment with multiple electrodes on a paddle-like distal end.
Figure 16B:
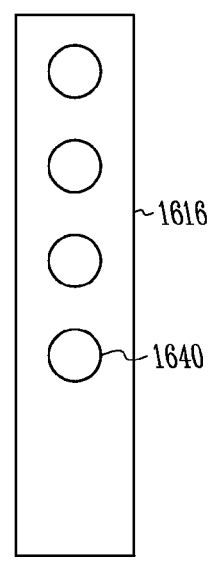

FIGS. 16A-16B illustrate a lead embodiment with multiple electrodes on a paddle-like distal end. The paddle-like distal end 1640 has a relatively flat profile. The electrodes 1616 are positioned on one side of the paddle, such that the electric stimulation field is generated on one side of the paddle-like distal end.

Figure 17:
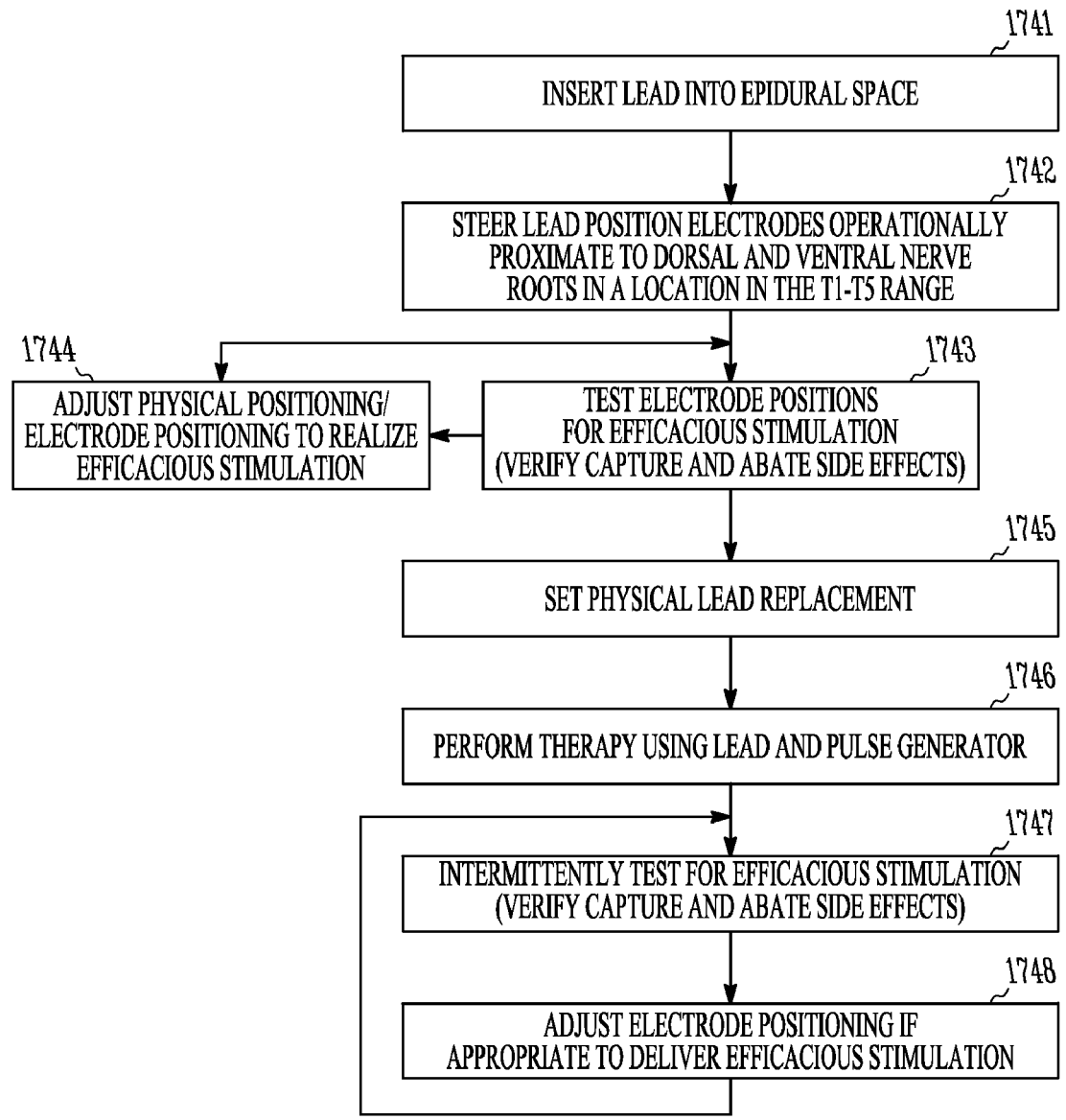
FIG. 17 illustrates a method embodiment to implant the spinal cord stimulation lead to establish and maintain efficacious stimulation therapy.

FIG. 17 illustrates a method embodiment to implant the spinal cord stimulation lead to establish and maintain efficacious stimulation therapy. At 1741, a lead is inserted into an epidural space. Examples were discussed with respect to FIG. 5 and with respect to various steerable lead and steerable catheter designs. At 1742, the lead (or catheter) is steered to direct the lead laterally adjacent to and at least partially around the spinal cord to position the electrodes on the lead operationally proximate to the dorsal and/or ventral nerve roots in a location in the T1-T5 range. At 1743, the electrode positions are tested to determine if the electrode positions provide efficacious stimulation. For example, some embodiments monitor one or more physiological parameters to verify capture of the neural target (e.g. ventral and/or dorsal nerve roots). The present subject matter is capable of selectively stimulating or targeting only the ventral nerve root and/or selectively stimulating the dorsal nerve root. Some embodiments monitor one or more physiological parameter to abate potential unintended responses to the neural stimulation. If unable to verify capture or if undesired side effects are present during the implantation process, the process adjusts the physical positioning and/or the electronic positioning in an effort to realize efficacious stimulation, as represented at 1744. The physical repositioning involves physically moving (e.g. pushing, pulling, rotating, contracting around spinal cord) the lead. The electronic repositioning involves selecting various combinations of electrodes to adjust the direction and position of the electric stimulation field. Electronic repositioning can be performed as part of an automatic process, where a device cycles through available electrode combinations (and stimulation intensity) until the desired efficacy is realized. Electronic repositioning can be controlled by a technician during the implant procedure. Some embodiments use a combination of technician control of potential configurations, and an automatic test routine.

When efficacious stimulation is detected, the physical lead placement is set at 1745. A proximal end of the lead is connected to an implantable pulse generator, which may be, for example, implanted in the small of the back. At 1746, therapy is delivered using the implanted lead and the implanted pulse generator. At 1747, the implanted pulse generator intermittently tests for efficacious stimulation to verify capture and/or abate side effects of the stimulation. If appropriate, the electronic positioning is adjusted to deliver efficacious stimulation, as illustrated at 1748. This electronic repositioning can be performed automatically, controlled by a technician using a programmer, or a combination thereof.

Figure 18:
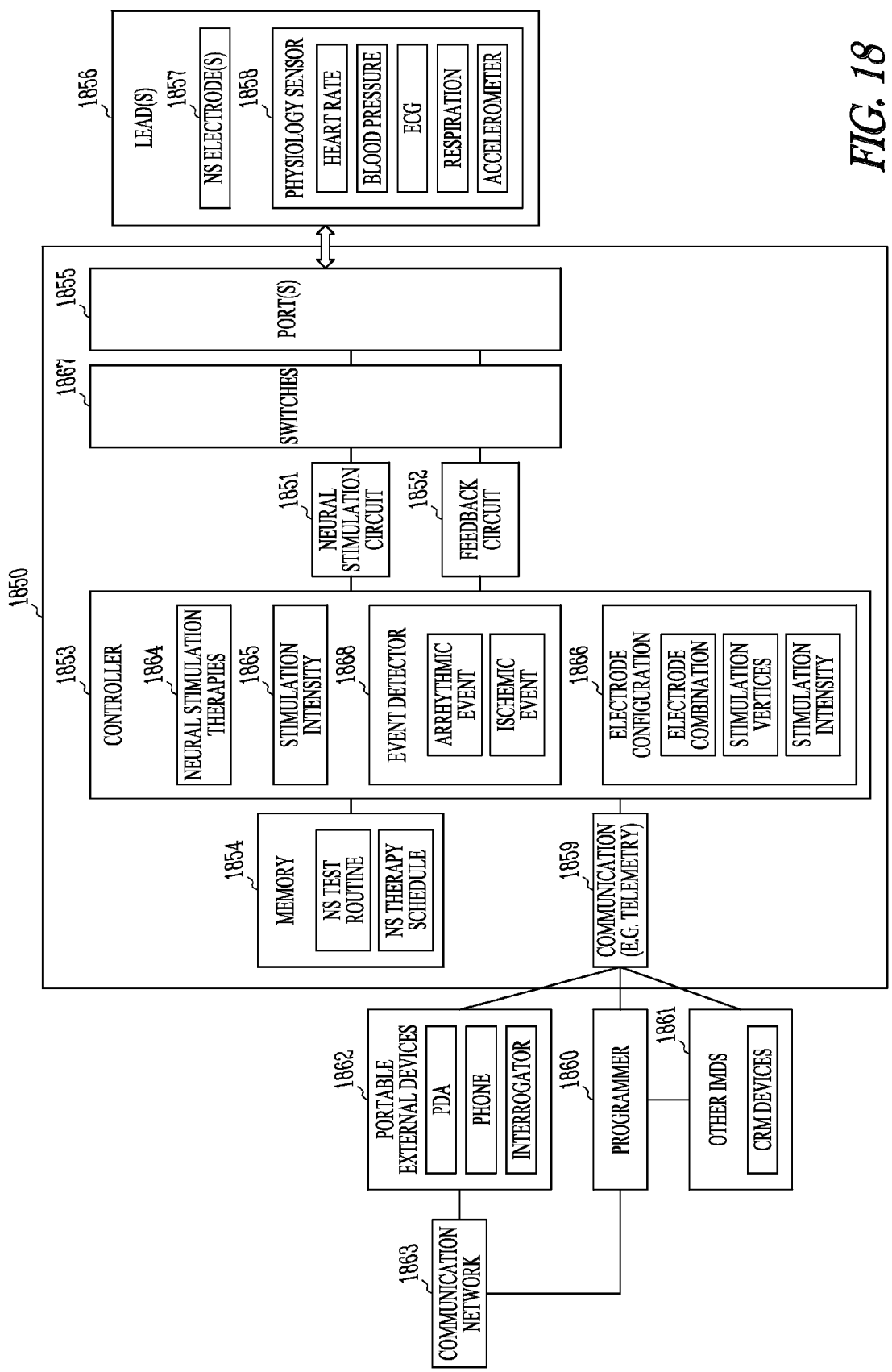
FIG. 18 illustrates a system used to deliver spinal cord stimulation, according to various embodiments.

FIG. 18 illustrates a system used to deliver spinal cord stimulation, according to various embodiments. The illustrated neural stimulator embodiment 1850 includes a neural stimulation circuit 1851, a feedback circuit 1852, a controller 1853, and memory 1854. The illustrated embodiment further includes at least one port 1855 to connect to at least one lead 1856. At least one lead is adapted to be fed into the dorsal epidural space to the T1-T5 region, and directed at least partially around the spinal cord to stimulate the ventral and/or dorsal nerve root. The neural stimulation circuit is connected to the port(s) to provide a neural stimulation signal to at least one neural stimulation electrode 1857 on the lead(s) to elicit a desired neural response when an appropriate signal is provided to an appropriately-positioned neural stimulation electrode. The feedback circuit is connected to the port(s) to receive a signal from the physiology sensor 1858. The physiology sensor may be on a different lead than the lead fed into the epidural space to stimulate the nerve root(s). Some embodiments receive a feedback signal from other implantable medical devices, such as a pacemaker or anti-arrhythmia device. The sensor senses a physiology function that depends, at least in part, on the neural stimulation. Examples of such functions includes heart rate, blood pressure, ECG waveforms, respiration, and acceleration/motion. Thus, various embodiments implement a heart rate sensor as the physiology sensor, and various embodiments implement a blood pressure sensor as the physiology sensor. One example of such a sensor is an acoustic sensor adapted to sense blood flow. The sensed blood flow is capable of being used to determine blood pressure and/or heart rate. However, other sensor technology can be used.

The illustrated system includes a communication module 1859 adapted to communicate with other devices. For example, some embodiments communicate using telemetry. Various embodiments wirelessly communicate from the implanted device to external devices, such as a programmer 1860. Various embodiments communicate, either through a wired connection or a wireless connection, to other implantable medical devices 1861. Example of other implantable medical devices include cardiac rhythm management devices, such as a pacemaker, cardiodefibrillator, and the like, and further include implantable neural stimulators. According to some embodiments, such other implantable medical devices sense physiological parameters that are affected by the stimulation of the nerve root, and communicate information regarding the sensed physiological parameters during an implant procedure or while the devices are chronically implanted in a patient. According to some embodiments, the communication module is adapted to communicate with a portable external device 1862, such as a personal data assistant, a telephone, an interrogator, a laptop computer. According to some embodiments, the portable external device 1862 and programmer 1860 are adapted to communicate over a communication network 1863.

Heart rate and/or blood pressure can be used to determine whether the stimulation is affecting the autonomic system. Additionally, various autonomic balance indicators (ABIs) can be used to provide feedback concerning the neural stimulation therapy directed toward the nerve root(s). Various embodiments assess ABI using one or various combinations of parameters, such as heart rate variability (HRV), heart rate turbulence (HRT), electrogram features, activity, respiration and activity. These parameters are briefly discussed below. Various embodiments provide closed loop control of the treatment using ABI.

HRV is one technique that has been proposed to assess autonomic balance. HRV relates to the regulation of the sinoatrial node, the natural pacemaker of the heart by the sympathetic and parasympathetic branches of the autonomic nervous system. An HRV assessment is based on the assumption that the beat-to-beat fluctuations in the rhythm of the heart provide us with an indirect measure of heart health, as defined by the degree of balance in sympathetic and vagus nerve activity.

The time interval between intrinsic ventricular heart contractions changes in response to the body's metabolic need for a change in heart rate and the amount of blood pumped through the circulatory system. For example, during a period of exercise or other activity, a person=s intrinsic heart rate will generally increase over a time period of several or many heartbeats. However, even on a beat-to-beat basis, that is, from one heart beat to the next, and without exercise, the time interval between intrinsic heart contractions varies in a normal person. These beat-to-beat variations in intrinsic heart rate are the result of proper regulation by the autonomic nervous system of blood pressure and cardiac output; the absence of such variations indicates a possible deficiency in the regulation being provided by the autonomic nervous system. One method for analyzing HRV involves detecting intrinsic ventricular contractions, and recording the time intervals between these contractions, referred to as the R-R intervals, after filtering out any ectopic contractions (ventricular contractions that are not the result of a normal sinus rhythm). This signal of R-R intervals is typically transformed into the frequency-domain, such as by using fast Fourier transform (FFT) techniques, so that its spectral frequency components can be analyzed and divided into low and high frequency bands. For example, the low frequency (LF) band can correspond to a frequency (f) range $0.04\ Hz<f<0.15\ Hz$, and the high frequency (HF) band can correspond to a frequency range $0.15\ Hz<f<0.40\ Hz$. The HF band of the R-R interval signal is influenced only by the parasympathetic/vagal component of the autonomic nervous system. The LF band of the R-R interval signal is influenced by both the sympathetic and parasympathetic components of the autonomic nervous system. Consequently, the ratio LF/HF is regarded as a good indication of the autonomic balance between sympathetic and parasympathetic/vagal components of the autonomic nervous system. An increase in the LF/HF ratio indicates an increased predominance of the sympathetic component, and a decrease in the LF/HF ratio indicates an increased predominance of the parasympathetic component. For a particular heart rate, the LF/HF ratio is regarded as an indication of patient wellness, with a lower LF/HF ratio indicating a more positive state of cardiovascular health. A spectral analysis of the frequency components of the R-R interval signal can be performed using a FFT (or other parametric transformation, such as autoregression) technique from the time domain into the frequency domain. Such calculations require significant amounts of data storage and processing capabilities. Additionally, such transformation calculations increase power consumption, and shorten the time during which the implanted battery-powered device can be used before its replacement is required.

One example of an HRV parameter is SDANN (standard deviation of averaged NN intervals), which represents the standard deviation of the means of all the successive 5 minutes segments contained in a whole recording. Other HRV parameters can be used.

HRT is the physiological response of the sinus node to a premature ventricular contraction (PVC), consisting of a short initial heart rate acceleration followed by a heart rate deceleration. HRT has been shown to be an index of autonomic function, closely correlated to HRV. HRT is believed to be an autonomic baroreflex. The PVC causes a brief disturbance of the arterial blood pressure (low amplitude of the premature beat, high amplitude of the ensuing normal beat). This fleeting change is registered immediately with an instantaneous response in the form of HRT if the autonomic system is healthy, but is either weakened or missing if the autonomic system is impaired.

By way of example and not limitation, it has been proposed to quantify HRT using Turbulence Onset (TO) and Turbulence Slope (TS). TO refers to the difference between the heart rate immediately before and after a PVC, and can be expressed as a percentage. For example, if two beats are evaluated before and after the PVC, TO can be expressed as:

$$TO\ \% = \frac{(RR_{+1}+RR_{+2})-(RR_{-2}+RR_{-1})}{(RR_{-2}+RR_{-1})}*100.$$

$RR_{-2}$ and $RR_{-1}$ are the first two normal intervals preceding the PVC and $RR_{+1}$ and $RR_{+2}$ are the first two normal intervals following the PVC. In various embodiments, TO is determined for each individual PVC, and then the average value of all individual measurements is determined. However, TO does not have to be averaged over many measurements, but can be based on one PVC event. Positive TO values indicate deceleration of the sinus rhythm, and negative values indicate acceleration of the sinus rhythm. The number of R-R intervals analyzed before and after the PVC can be adjusted according to a desired application. TS, for example, can be calculated as the steepest slope of linear regression for each sequence of five R-R intervals. In various embodiments, the TS calculations are based on the averaged tachogram and expressed in milliseconds per RR interval. However, TS can be determined without averaging. The number of R-R intervals in a sequence used to determine a linear regression in the TS calculation also can be adjusted according to a desired application.

Rules or criteria can be provided for use to select PVCs and for use in selecting valid RR intervals before and after the PVCs. A PVC event can be defined by an R-R interval in some interval range that is shorter than a previous interval by some time or percentage, or it can be defined by an R-R interval without an intervening P-wave (atrial event) if the atrial events are measured. Various embodiments select PVCs only if the contraction occurs at a certain range from the preceding contraction and if the contraction occurs within a certain range from a subsequent contraction. For example, various embodiments limit the HRT calculations to PVCs with a minimum prematurity of 20% and a post-extrasystole interval which is at least 20% longer than the normal interval. Additionally, pre-PVC R-R and post-PVC R-R intervals are considered to be valid if they satisfy the condition that none of the beats are PVCs. One HRT process, for example, excludes RR intervals that are less than a first time duration, that are longer than a second time duration, that differ from a preceding interval by more than a third time duration, or that differ from a reference interval by a predetermined amount time duration or percentage. In an embodiment of such an HRT process with specific values, RR intervals are excluded if they are less than 300 ms, are more than 2000 ms, differ from a preceding interval by more than 200 ms, or differ by more than 20% from the mean of the last five sinus intervals. Various embodiments of the present subject matter provide programmable parameters, such as any of the parameters identified above, for use in selecting PVCs and for use in selecting valid RR intervals before and after the PVCs.

Benefits of using HRT to monitor autonomic balance include the ability to measure autonomic balance at a single moment in time. Additionally, unlike the measurement of HRV, HRT assessment can be performed in patients with frequent atrial pacing. Further, HRT analysis provides for a simple, non-processor-intensive measurement of autonomic balance. Thus, data processing, data storage, and data flow are relatively small, resulting in a device with less cost and less power consumption. Also, HRT assessment is faster than HRV, requiring much less R-R data. HRT allows assessment over short recording periods similar in duration to typical neural stimulation burst durations, such as on the order of tens of seconds, for example.

Various embodiments extract various ECG features to provide an ABI. Examples of such features include heart rate, which can be used to form HRV, and HRT. Other features can be extracted from the ECG, and one or various combinations of these features can be used to provide an ABI. Various embodiments provide blood pressure to provide an ABI. For example, some embodiments sense pulmonary artery blood pressure.

Activity sensors can be used to assess the activity of the patient. Sympathetic activity naturally increases in an active patient, and decreases in an inactive patient. Thus, activity sensors can provide a contextual measurement for use in determining the autonomic balance of the patient. Various embodiments, for example, provide a combination of sensors to trend heart rate and/or respiration rate to provide an indicator of activity.

Two methods for detecting respiration involve measuring a transthoracic impedance and minute ventilation. Respiration can be an indicator of activity, and can provide an explanation of increased sympathetic tone. For example, it may not be appropriate to change or modify a treatment for modulating autonomic tone due to a detected increase in sympathetic activity attributable to exercise.

Respiration measurements (e.g. transthoracic impedance) can also be used to measure Respiratory Sinus Arrhythmia (RSA). RSA is the natural cycle of arrhythmia that occurs through the influence of breathing on the flow of sympathetic and vagus impulses to the sinoatrial node. The rhythm of the heart is primarily under the control of the vagus nerve, which inhibits heart rate and the force of contraction. The vagus nerve activity is impeded and heart rate begins to increase when a breath is inhaled. When exhaled, vagus nerve activity increases and the heart rate begins to decrease. The degree of fluctuation in heart rate is also controlled significantly by regular impulses from the baroreceptors (pressure sensors) in the aorta and carotid arteries. Thus, a measurement of autonomic balance can be provided by correlating heart rate to the respiration cycle.

The memory 1854 includes computer-readable instructions that are capable of being operated on by the controller to perform functions of the device. Thus, in various embodiments, the controller is adapted to operate on the instructions to provide programmed neural stimulation therapies 1864 according to a neural stimulation therapy schedule stored in the memory. Various "closed loop" systems vary the intensity of the neural stimulation, as generally illustrated by the stimulation intensity module 1865, based on the sensed physiology signal received by the feedback circuit according to a preprogrammed therapy to provide a desired affect. Thus, the closed loop system is capable of reducing and increasing the neural stimulation intensity as appropriate to maintaining some measured physiological parameters within an upper and lower boundary during the neural stimulation therapy. Various "open loop" systems without feedback from the physiology signal also can be programmed to vary the stimulation intensity. For example, intensity can be modulated based on a programmed schedule. Various embodiments modulate the stimulation intensity by modulating the amplitude of the neural stimulation signal, the frequency of the neural stimulation signal, the duty cycle of the neural stimulation signal, the duration of a stimulation signal, the waveform of the neural stimulation signal, the polarity of the neural stimulation signal, or any combination thereof.

Various embodiments automatically change the electrode configuration, as generally illustrated by the electrode configuration module 1866 of the controller 1853. The illustrated electrode configuration module is adapted to control switches 1867 to control which electrodes of the available electrodes are used to deliver the neural stimulation, and the stimulation vectors for the electrodes. Additionally, the illustrated electrode configuration module is adapted to work with the stimulation intensity module to control the stimulation intensity for the different electrode combinations and stimulation vectors. Thus, for example, the electrode configuration module can find a reference neural stimulation level for a particular electrode combination and vector, and the stimulation intensity module can further modulate the neural stimulation based on the reference neural stimulation level. A neural stimulation test routine stored in the memory controls the process of testing for a efficacious electrode configuration from the available electrode configurations.

In various embodiments, the controller automatically implements the neural stimulation test routine, such as in a chronically-implanted device. In various embodiments, the controller and a user interface cooperate to implement a neural stimulation test routine to allow a user to select the at least one of the neural stimulation electrodes to use in delivering the autonomic neural stimulation therapy, such as maybe used in a device to implant the lead into the desired position to stimulate the desired nerve root(s). For example, during an implantation procedure, the user interface can display test results for various electrode configurations. The information identifying the electrode configurations can include the electrodes used in the stimulation, the stimulation amplitude, the stimulation frequency, the stimulation duty cycle, the stimulation duration, the stimulation waveform, and the stimulation polarity. The test results can include the detected physiologic response (e.g. heart rate) attributed to the neural stimulation for an electrode configuration. The user can review the test results, and select an electrode configuration using the test results.

The illustrated controller includes an event detector 1868, such as may be used to detect an arrhythmic event or an ischemic event. Upon the detection of an event, the device appropriately adjusts the therapy for the event. According to some embodiments, another IMD 1861 detects the event and communicates the event to the device to adjust the stimulation of the ventral and/or dorsal nerve roots.

Neural Stimulation Therapies

Examples of neural stimulation therapies include neural stimulation therapies for blood pressure control such as to treat hypertension, for cardiac rhythm management, for myocardial infarction and ischemia, for heart failure, and for pain control. A therapy embodiment involves preventing and/or treating ventricular remodeling. Activity of the autonomic nervous system is at least partly responsible for the ventricular remodeling which occurs as a consequence of an MI or due to heart failure. It has been demonstrated that remodeling can be affected by pharmacological intervention with the use of, for example, ACE inhibitors and beta-blockers. Pharmacological treatment carries with it the risk of side effects, however, and it is also difficult to modulate the effects of drugs in a precise manner. Embodiments of the present subject matter employ electrostimulatory means to modulate autonomic activity, referred to as anti-remodeling therapy or ART. When delivered in conjunction with ventricular resynchronization pacing, also referred to as remodeling control therapy (RCT), such modulation of autonomic activity may act synergistically to reverse or prevent cardiac remodeling.

One neural stimulation therapy embodiment involves treating hypertension by increasing parasympathetic tone (e.g. inhibiting sympathetic activity) for sustained periods of time sufficient to reduce hypertension. Neural stimulation (e.g. sympathetic nerve stimulation and/or parasympathetic nerve inhibition) can mimic the effects of physical conditioning. It is generally accepted that physical activity and fitness improve health and reduce mortality. Studies have indicated that aerobic training improves cardiac autonomic regulation, reduces heart rate and is associated with increased cardiac vagal outflow. A baseline measurement of higher parasympathetic activity is associated with improved aerobic fitness. Exercise training intermittently stresses the system and increases the sympathetic activity during the stress. However, when an exercise session ends and the stress is removed, the body rebounds in a manner that increases baseline parasympathetic activity and reduces baseline sympathetic activity. Conditioning can be considered to be a repetitive, high-level exercise that occurs intermittently over time. A conditioning therapy that provides intermittent stress can be applied as therapy for heart failure.

Neural targets in the spinal column can be targeted as part of a therapy for pain control. The pain control therapy can be used to address somatic pain, visceral pain or neuropathic pain. The pain control therapy can also be used to address acute or chronic pain. According to various embodiments, pain control therapies are integrated with other therapies (e.g. heart failure). Some embodiments provide means for a patient to activate the pain control therapy. This means may use a wireless communication from an external device to the implantable pulse generator, or a magnetic field such as from a magnet positioned over the implantable pulse generator. By way of example, a patient who is experiencing an episode of angina pain may choose to initiate a pain control therapy. A physician can program limits on the requested pain control therapy, so as to limit the number of times the therapy can be requested over a period of time. Various embodiments implement the pain control therapy in conjunction with another therapy to avoid or minimize pain with the therapy. For example, if a defibrillation shock is going to be applied to a patient, various embodiment implement pain control therapy in anticipation of delivering the shock.

Myocardial Stimulation Therapies

Various neural stimulation therapies can be integrated with various myocardial stimulation therapies. The integration of therapies may have a synergistic effect. Therapies can be synchronized with each other, and sensed data can be shared. A myocardial stimulation therapy provides a cardiac therapy using electrical stimulation of the myocardium. Some examples of myocardial stimulation therapies are provided below.

A pacemaker is a device which paces the heart with timed pacing pulses, most commonly for the treatment of bradycardia where the ventricular rate is too slow. If functioning properly, the pacemaker makes up for the heart's inability to pace itself at an appropriate rhythm in order to meet metabolic demand by enforcing a minimum heart rate. Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

CRT can be beneficial in reducing the deleterious ventricular remodeling which can occur in post-MI and heart failure patients. Presumably, this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle near the infarcted region in a manner which may cause a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected.

One of ordinary skill in the art will understand that, the modules and other circuitry shown and described herein can be implemented using software, hardware, and combinations of software and hardware. As such, the terms module and circuitry, for example, are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a computer data signal embodied in a carrier wave or propagated signal, that represents a sequence of instructions which, when executed by one or more processors cause the processor(s) to perform the respective method. In various embodiments, the methods are implemented as a set of instructions contained on a computer-accessible medium capable of directing a processor to perform the respective method. In various embodiments, the medium is a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for using a neural stimulation lead fed vertically through a dorsal epidural space of a human and at least partially wrapped around a spinal cord to operably position a first electrode proximate to a ventral nerve root and operably position a second electrode proximate to a dorsal nerve root, the method comprising delivering electrical stimulation pulses to at least one of:
   the ventral nerve root using a first conductor in the lead electrically connected to the first electrode to stimulate or inhibit efferent sympathetic activity from the ventral nerve root; or
   the dorsal nerve root using a second conductor in the lead electrically connected to the second electrode to stimulate afferent sympathetic activity from the dorsal nerve root, wherein the first conductor is distinct from the second conductor,
   the method further comprising alternating delivery of electrical stimulation to the ventral nerve root and delivery of electrical stimulation to the dorsal nerve root.

2. The method of claim 1, wherein delivering electrical stimulation pulses includes delivering neural stimulation based on a manual, patient-initiated input.

3. The method of claim 1, further comprising changing a frequency of the electrical stimulation to a first frequency range to inhibit sympathetic activity and to a second frequency range distinct from the first frequency range to stimulate sympathetic activity.

4. The method of claim 1, wherein the neural stimulation lead is at least partially wrapped around a spinal cord proximate to a vertebrae corresponding to at least one of T1, T2, T3, T4 or T5.

5. The method of claim 1, further comprising sensing at least one parameter to verify capture of a desired neural target.

6. The method of claim 5, wherein, if the capture of the desired neural target is not verified, automatically repositioning the neural stimulation field.

7. The method of claim 6, wherein automatically repositioning the neural stimulation field includes automatically changing stimulation vectors.

8. The method of claim 6, wherein automatically repositioning the neural stimulation field includes automatically changing stimulation intensity.

9. The method of claim 1, wherein delivering electrical stimulation pulses includes using an implantable system to deliver electrical stimulation pulses to at least one of the ventral nerve root or the dorsal nerve root.

10. The method of claim 1, wherein the neural stimulation lead includes a distal end with a plurality of electrodes, the method further comprising selecting combinations of the plurality of electrode for use to deliver electrical stimulation pulses.

11. The method of claim 1, further comprising intermittently testing an efficacy of the electrical stimulation pulses.

12. The method of claim 1, further comprising determining whether a predetermined event occurred, and adjusting stimulation based on whether the predetermined event occurred.

13. The method of claim 1, wherein the predetermined event includes an arrhythmic event, an ischemic event or experienced pain.

14. The method of claim 1, wherein delivering electrical stimulation pulses includes delivering electrical stimulation pulses according to a programmed schedule.

15. A method for using a neural stimulation lead fed vertically through a dorsal epidural space of a human and at least partially wrapped around a spinal cord to operably position a first electrode proximate to a ventral nerve root and operably position a second electrode proximate to a dorsal nerve root, the method comprising delivering electrical stimulation pulses to at least one of:
   the ventral nerve root using a first conductor in the lead electrically connected to the first electrode to stimulate or inhibit efferent sympathetic activity from the ventral nerve root; or
   the dorsal nerve root using a second conductor in the lead electrically connected to the second electrode to stimulate afferent sympathetic activity from the dorsal nerve root, wherein the first conductor is distinct from the second conductor,
   the method further comprising:
   intermittently delivering electrical stimulation pulses to the ventral nerve root;
   sensing an event; and
   in response to the sensed event,
      delivering electrical stimulation pulses to the dorsal oot to stimulate afferent sympathetic activity, or
      delivering electrical stimulation pulses to the ventral nerve root to inhibit efferent sympathetic activity.

16. The method of claim 15, wherein the sensed event is a tachyarrhythmia.

\* \* \* \* \*